United States Patent
Cutrone et al.

(10) Patent No.: US 7,256,024 B2
(45) Date of Patent: Aug. 14, 2007

(54) TYRISSAMYCIN ANTIBIOTIC

(75) Inventors: Jingfang Q. Cutrone, Wallingford, CT (US); Lyndon M. Foster, Oceanside, CA (US); Kimberly D. Krampitz, Southington, CT (US); Stephen W. Mamber, Pawtucket, RI (US); Grace A. McClure, Northford, CT (US); Todd C. Peterson, Coronado, CA (US); Lisa C. Rupar, Woodbury, CT (US); Katie A. Thompson, Milford, IA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 393 days.

(21) Appl. No.: 10/891,888

(22) Filed: Nov. 18, 2004

(65) Prior Publication Data

US 2005/0064568 A1    Mar. 24, 2005

Related U.S. Application Data

(60) Continuation-in-part of application No. 09/968,598, filed on Oct. 1, 2001, now abandoned, which is a division of application No. 09/378,309, filed on Aug. 20, 1999, now Pat. No. 6,328,961.

(60) Provisional application No. 60/097,214, filed on Aug. 20, 1998.

(51) Int. Cl.
*C12P 7/62* (2006.01)
*A61K 35/66* (2006.01)
*A61K 35/74* (2006.01)

(52) U.S. Cl. ............... 435/135; 424/115; 424/116; 560/130; 435/253.5; 435/108; 435/170; 435/41

(58) Field of Classification Search ............... None
See application file for complete search history.

(56) References Cited

U.S. PATENT DOCUMENTS 5,824,485 A    10/1998    Thompson et al.

*Primary Examiner*—Irene Marx
(74) *Attorney, Agent, or Firm*—David M. Morse; Pamela A. Mingo

(57) ABSTRACT

A novel tyrosyl diester antibiotic is obtained from fermentation of a recombinant strain of *Streptomyces lividans* designated *Stretomyces lividans* WD 15684 (ATCC-202143). The new antibiotic, designated tyrissamycin, exhibits antibacterial activity, particularly against gram-positive bacteria.

2 Claims, 4 Drawing Sheets

TYRISSAMYCIN ANTIBIOTIC

CROSS-REFERENCE TO RELATED APPLICATION

This application is a continuation in part of U.S. application Ser. No. 09/968,598, filed Oct. 1, 2001, now abandoned which is a Divisional of U.S. application Ser. No. 09/378,309, filed Aug. 20, 1999, now U.S. Pat. No. 6,328,961, which claims priority to U.S. Provisional Application Ser. No. 60/097,214 filed Aug. 20, 1998.

BACKGROUND OF THE INVENTION

Field of the Invention

This invention relates to a novel tyrosyl diester antibacterial antibiotic designated by the present inventors as tyrissamycin which may be obtained by cultivation of a strain of Streptomyces lividans. The antibiotic provided by the present invention has antibacterial activity against a variety of gram-positive bacteria.

SUMMARY OF THE INVENTION

Figure 1:
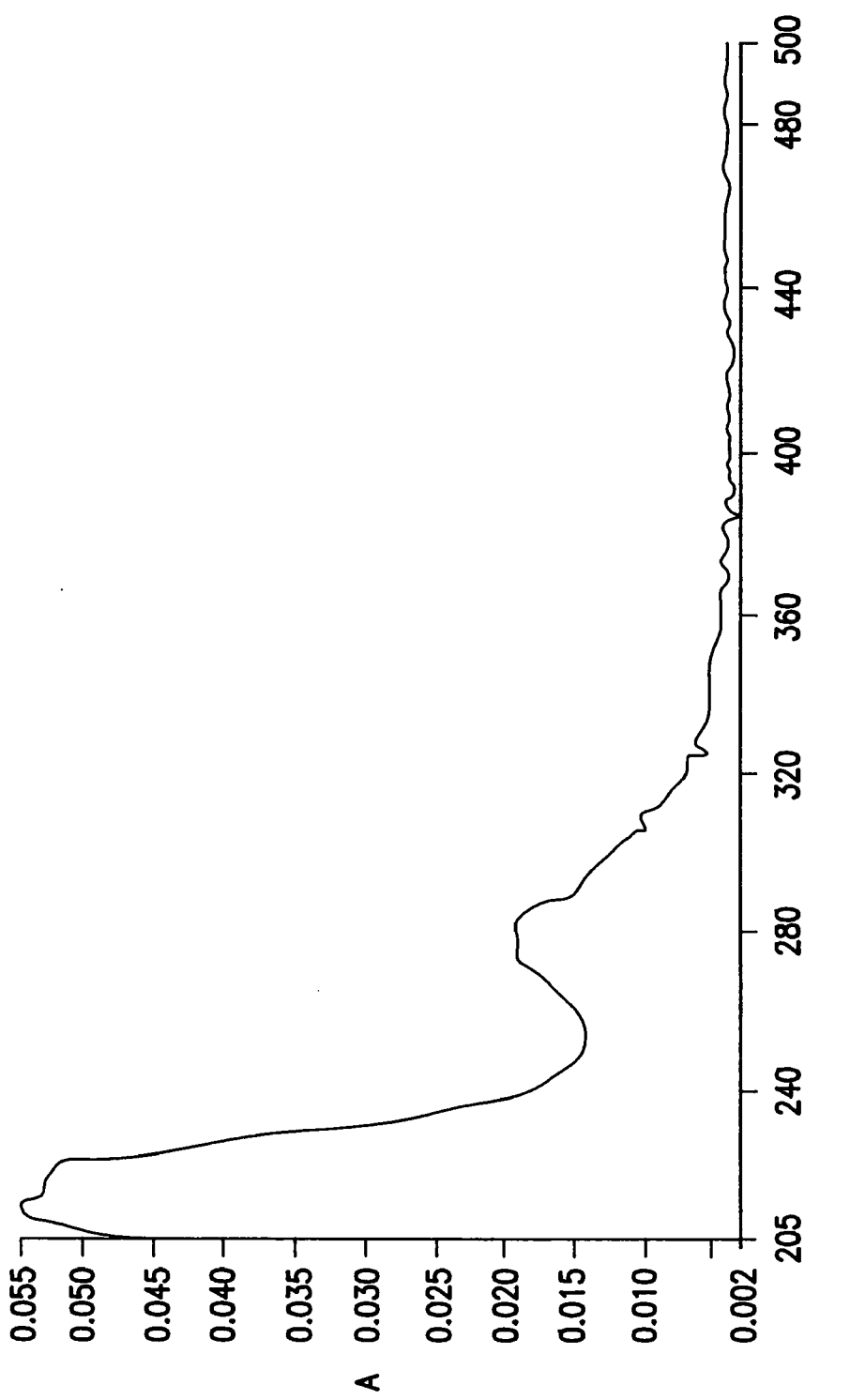
FIG. 1 shows the ultraviolet absorption spectrum of tyrissamycin in methanol.

The present invention provides the novel antibacterial antibiotic designated by the present inventors as tyrissamycin and a fermentation process for production of this antibiotic using a novel recombinant strain of Streptomyces lividans designated herein as Streptomyces lividans WD 15684 (ATCC-202143). The antibiotic of the present invention has been found to be useful for the treatment of a variety of bacterial diseases caused by gram-positive bacteria.

Also provided are pharmaceutical compositions of tyrissamycin, a method for the treatment of bacterial diseases in animals using tyrissamycin or a pharmaceutical composition thereof, and a fermentation process for obtaining the antibiotic.

DETAILED DESCRIPTION OF THE INVENTION

The tyrissamycin antibiotic of the present invention may be prepared by fermentation of a tyrissamycin-producing strain of Streptomyces lividans. The preferred producing organism is a novel strain of Streptomyces lividans TK-64 designated herein as Streptomyces lividans WD 15684. The organism was isolated as a recombinant streptomycete using the procedures described in published application WO 96/34112 and in Chapter 12, pages 71-76, Proceedings from the Genetics and Molecular Biology of Industrial Microorganisms (GMBIM) Conference, 1997, edited by Richard H. Baltz, George D. Hegeman and Paul L. Skatrud. Briefly, DNA was isolated from one or more actinomycetes, none of which were Streptomyces lividans. The actinomycete DNA was inserted into plasmids which were used to transform Streptomyces lividans TK-64. A biologically pure culture of the resulting recombinant strain WD 15684 has been deposited with the American Type Culture Collection, 10801 University Boulevard, Manassas, Va. 20110-2209, and added to its permanent collection of microorganisms as ATCC-202143. The culture is also maintained as a dormant culture in lyophile tubes and cryogenic vials in the Bristol-Myers Squibb Pharmaceutical Research Institute Culture Collection, 5 Research Parkway, Wallingford, Conn. 06492. The results of taxonomic studies performed on strain WD 15684 confirm that it is a strain of Streptomyces lividans.

It is to be understood that for the production of tyrissamycin the present invention, although described in detail with reference to the preferred producing strain Streptomyces lividans WD 15684, is not intended to be limited to this microorganism. It is specifically intended that the invention embrace strain WD 15684 and all tyrissamycin-producing variants and mutants thereof which may be obtained by methods well known to those skilled in the art, e.g., by subjecting the deposited microorganism to x-rays or ultraviolet radiation, nitrogen mustard, phage exposure, and the like.

The tyrissamycin antibiotic may be produced by cultivating a tyrissamycin-producing strain of Streptomyces lividans, preferably a strain having the identifying characteristics of Streptomyces lividans ATCC-202143, or a mutant or variant thereof, under submerged aerobic conditions in an aqueous nutrient medium containing assimilable sources of carbon and nitrogen until a substantial amount of tyrissamycin is produced by said organism in said culture medium. The tyrissamycin so obtained may be isolated from the fermentation medium in substantially pure form by conventional procedures such as those described in the examples which follow. Tyrissamycin exhibits antibacterial activity in standard antibacterial model systems.

The producing organism is grown in a nutrient medium containing an assimilable source of carbon such as glucose, cellobiose, trehalose, potato starch, glycerol or ribose. The medium should also contain an assimilable source of nitrogen such as fishmeal, peptone, peanut meal, cottonseed meal or cornsteep liquor. Nutrient inorganic salts can also be incorporated in the medium so as to provide sodium, potassium, ammonium, calcium, phosphate, nitrate, chloride, bromide, carbonate and like ions. Trace elements such as copper, manganese, iron, zinc, etc. are added to the medium if desired, or they may be present as impurities of other constituents of the medium.

Production of the tyrissamycin antibiotic may be effected at any temperature conducive to satisfactory growth of the organism, i.e., 22° C. to 42° C., and is conveniently carried out at a temperature of about 32° C. The fermentation may be carried out in shake flasks or in laboratory or industrial fermentors of various capacities. When tank fermentation is to be used, it is desirable to produce a vegetative inoculum in a nutrient broth by inoculating a small volume of the culture medium with a slant, a cryopreservative culture or a lyophilized culture of the producing organism. After obtaining a viable and active inoculum in this manner, it is transferred aseptically to the fermentation tank charged with production medium for large scale production of tyrissamycin. The medium in which the vegetative inoculum is prepared can be the same as or different from that used in the tank as long as it is such that a good growth of the producing organism can be obtained. Further agitation may be provided by a mechanical impeller. Antifoam agents such as lard oil or silicone oil may also be added if needed. Antibiotic production may be monitored by thin layer chromatography (TLC) assay, TLC bioautographic assay, column chromatographic assay, high performance liquid chromatography (HPLC) assay, or by conventional biological assay.

When the fermentation is complete, the tyrissamycin antibiotic is extracted from the culture broth with a suitable organic solvent such as ethyl acetate or 1-butanol and the antibiotic recovered by the extract and purified by conventional isolation procedures.

Physico-chemical Properties

A purified sample of tyrissamycin was isolated as a white amorphous powder. Other characterizing properties of the antibiotic are as follows:

Solubility: Soluble in chloroform, dimethylsulfoxide (DMSO), and methanol and practically insoluble in water.

Ultraviolet Spectrum: UV max $_{MeOH}$ (Absorbtivity): 212 (4.7), 219 (sh. 4.6), 278 (1.6) nm (FIG. 1)

Figure 2:
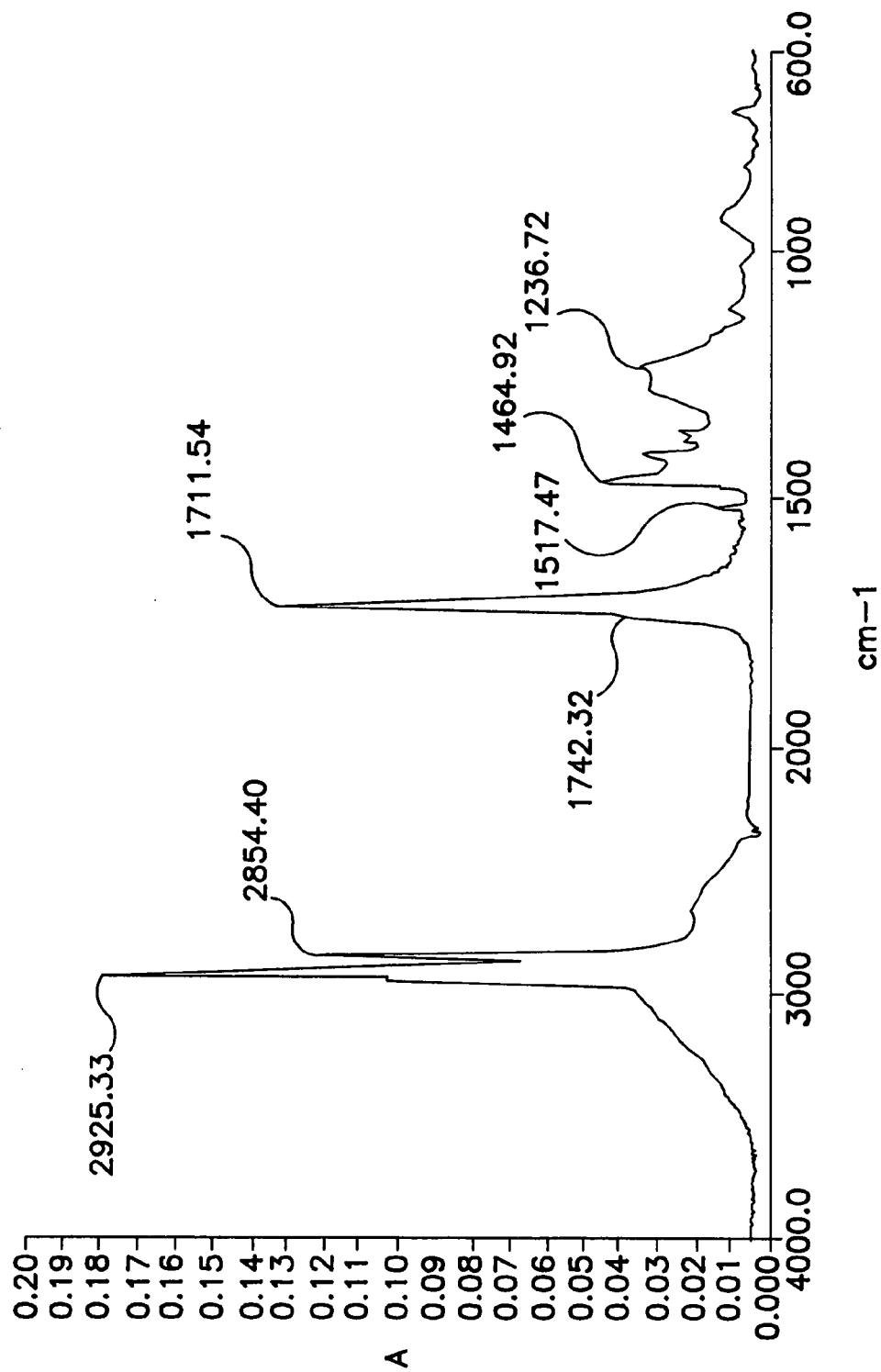
FIG. 2 shows the infrared absorption spectrum of tyrissamycin (KBr pellet).

Infrared Spectrum: Major Bands (cm$^{-1}$) 2925, 2854, 1742, 1711, 1517, 1465, 1237 cm$^{-1}$ (FIG. 2)

Figure 3:
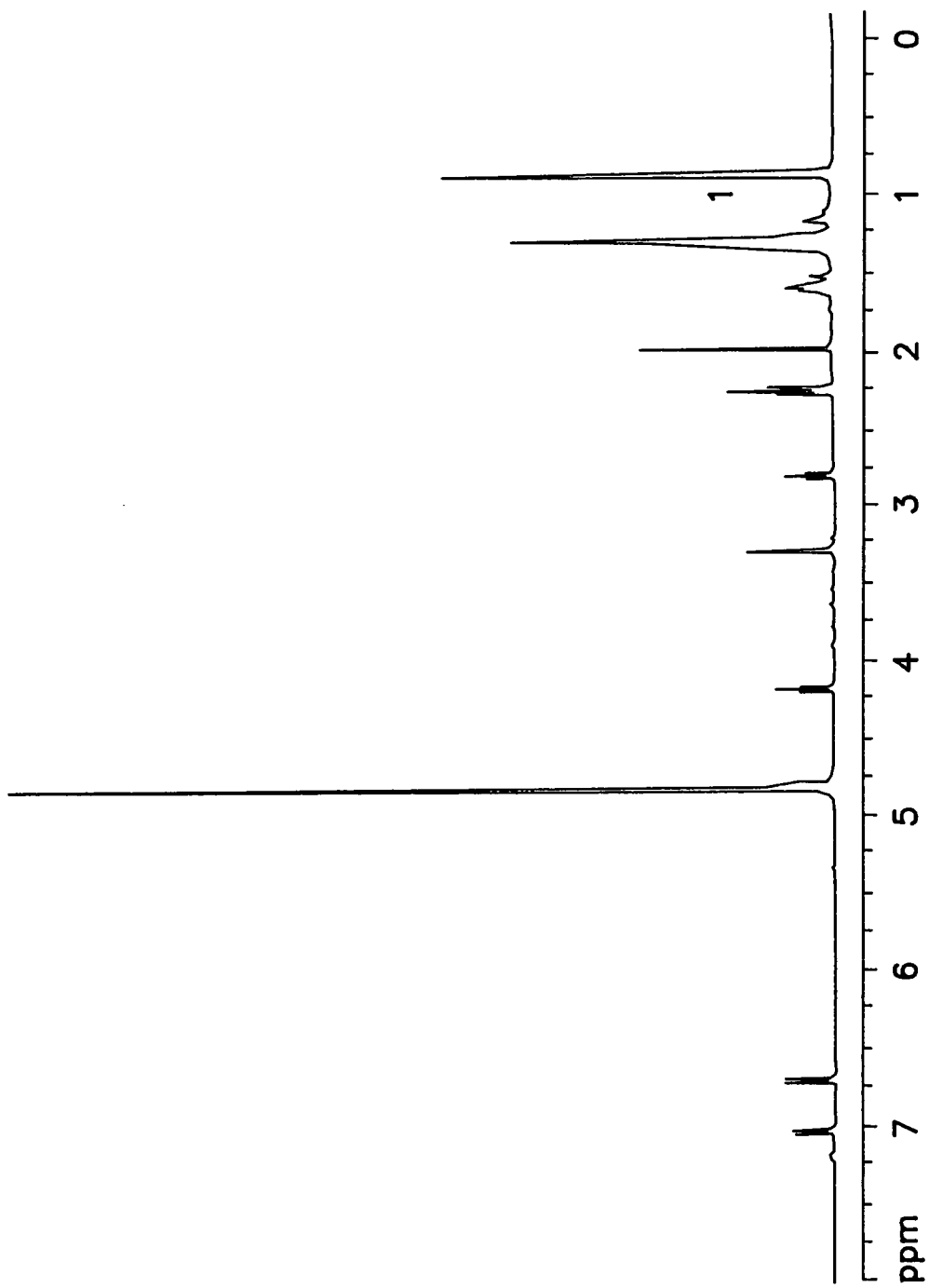
FIG. 3 shows the $^1$H NMR spectrum of tyrissamycin in $CD_3OD$.

$^1$H-NMR: See. FIG. 3 (CD$_3$OD)

$^{13}$C-NMR: See FIG. 4 (CD$_3$OD)

Based on the above properties, the structure of tyrissamycin is believed to be

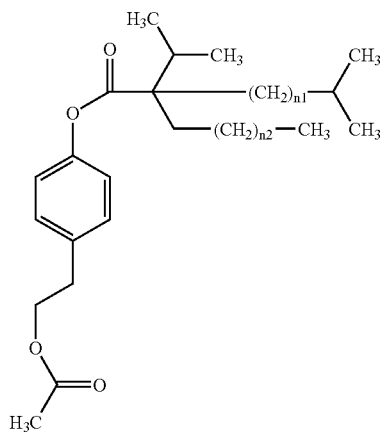

$n_1$ and $n_2$ represent alkylene chains of unknown length

Biological Properties:

Tyrissamycin was evaluated in vitro to detemine the minimal inhibitory concentrations (MIC) against seven gram-positive bacteria using the microtiter dilution technique. This method is described by T. B. Conrath, "Handbook of Microtiter Procedures," Dynatech Corp., Cambridge, Mass., USA (1972); and T. L. Gavan et al "Microdilution Test Procedures," in *Manual of Clinical Microbiology*, E. H. Lennette, Ed., American Soc. for Microbiol., Washington, D.C., USA (1980). These tests are performed in accordance with procedures established by the National Committee on Clinical Laboratory Standards (NC-CLS). The test procedure is as follows: Each well of a sterile 96-well microdilution tray is filled under aseptic conditions with 0.1 ml of Mueller-Hinton broth. A 0.05-ml sample of the test compound solution is added to a well in the first row of the tray. A microdilutor apparatus is used to simultaneously mix the contents of these wells and to transfer aliquots to each succeeding row of cells to obtain a range of serially diluted solutions. The last row of wells is untreated and serves as a control. Each well containing broth and test compound is inoculated with about ten microliters of inoculum of a given test microorganism. One well in the last row of wells (which is free of test compound) is not inoculated and is used as a sterility control. The trays are sealed and incubated at 37° C. for 16-24 hours. After the incubation period, each plate is evaluated by determining the lowest concentration of test compound that visibly inhibits the growth of a given microorganism and recorded as the minimal inhibitory concentration in µg/ml.

The antimicrobial activity of tyrissamycin is reported in Table 1.

TABLE 1

Antibacterial Activity of Tyrissamycin

| Microorganism | Minimal Inhibitory Concentration, µg/ml |
|---|---|
| *Streptococcus pneumoniae* | 4 |
| *Streptococcus pyogenes* | 4 |
| *Enterococcus faecalis* | 32 |
| *Enterococcus faecium* | 64 |
| *Staphylococcus aureus* | 32 |
| *Staphylococcus epidermidis* | 32 |
| *Staphylococcus haemolyticus* | 32 |

As indicated above, the antibiotic of the present invention is useful as an antimicrobial agent, having utility in inhibiting, including killing, the growth of microorganisms. It is particularly useful as an antibacterial agent, especially against gram-positive bacteria such as those of the genera *Streptococcus, Enterococcus*, and *Staphylococcus*.

The compound may, for example, be used in a method for treating a host infected by a bacterium or in preventing infection of said host by said bacterium, comprising administering to said host tyrissamycin in an amount effective for said prevention or treatment.

Hosts include animals, particular mammals such as dogs, cats and other domestic mammals, and, especially, humans. The dosage form and mode of administration, as well as the dosage amount, may be selected by one skilled in the art. The dosage amount will vary with the severity of the infection, and with the size and species of the host. Daily dosages for an adult human may be determined by methods known to one of ordinary skill in the art. Administration to a mammalian host may, for example, be oral, topical, rectal, or parenteral.

Pharmaceutical compositions are also provided by the present invention which comprise tyrissamycin in an amount effective for the prevention or treatment of infection by a bacterium and a pharmaceutically acceptable carrier or diluent. The appropriate solid or liquid vehicle or diluent may be selected, and the compositions prepared, by methods known to one of ordinary skill in the art. Examples of such compositions include solid compositions for oral administration such as solutions, suspensions, syrups, or elixirs and preparations for parenteral administration such as sterile solutions, suspensions, or emulsions. They may also be manufactured in the form of sterile solid compositions which can be dissolved in sterile water, physiological saline, or some other suitable sterile injectable medium immediately before use. The pharmaceutical compositions may contain other antibacterial agents.

The compound of the present invention may also be employed as an antimicrobial agent useful in inhibiting the growth of, including killing, microorganisms present on a surface or in a medium outside a living host. The present invention, therefore, provides a method for inhibiting the growth of bacteria present on a surface or in a medium, comprising the step of contacting the surface or medium with tyrissamycin in an amount effective for the inhibition. Thus, the antibiotic of the present invention may be employed, for example, in disinfectants for surface treatment, such as disinfection of surgical instruments, or as preservatives for a variety of solid and liquid media susceptible to microbial growth. Suitable amounts of the antibiotic may be determined by methods known to one of ordinary skill to the art. Compositions comprising tyrissamycin in an amount effective for inhibiting the growth of bacteria, and a vehicle or diluent, are also provided by the present invention.

The following example is provided for illustrative purposes only and is not intended to limit the scope of the method.

EXAMPLE 1

Preparation of Tyrissamycin

General Methods:

Materials:

Hexanes, chloroform, (anhydrous ACS grade), methanol, acetonitrile (anhydrous HPLC grade) and water were not repurified or redistilled. Sephadex LH-20 was purchased from Pharmacia LKB, Uppsala, Sweden.

Analytical Thin Layer Chromatography (TLC):

Silica gel precoated thin layer chromatography plates, Kieselgel 60 F254 on aluminum sheet, 5×20 cm, 0.2 mm, were purchased from EM Separations, Gibbstown, N.J. The plates were developed in a tank equilibrated with toluene/ethyl acetate (1:2 v/v). The components of the resulting chromatogram were detected under a UV light, and visualized by phosphomolybidic acid followed by prolonged heating.

Preparative TLC:

Silica gel precoated Kieselgel 60 F254 plates on glass, 20×20 cm, 2 mm, purchased from EM Separations, were used for preparative purification. The plates were developed in a tank equilibrated with toluene/ethyl acetate (1:2 v/v). The components of the resulting chromatogram were detected under a UV light. The silica band containing the components was scraped and pressed to a fine powder, followed by elution with chloroform/methanol (4:1, v/v). The eluant was then evaporated in vacuo to dryness.

Analytical HPLC:

The purification of tyrissamycin was monitored by HPLC analysis on a Microsorb-MV 5 m C-18 column, 4.6 mm i.d.×25 cm 1. (Rainin Instrumnet Company, Inc., Woburn, Mass.). Analyses were done on a Hewlett Packard 1090 Liquid Chromatograph, equipped with a model photodiode array spectrophotometer set at 254 and 280 nm, and HPLC[3D] ChemStation operating software. A gradient solvent system and 0.01 M potassium phosphate buffer (pH 3.5) was used, according to the method of D. J. Hook et al (J. Chromatogr. 385, 99, 1987). The eluant was pumped at a flow rate of 1.2 ml/min.

Analytical Instrumentation:

$^1$H-NMR and $^{13}$C-NMR spectra were obtained on a Bruker AM-500 500 MHz instrument operating at 500.13 and 125.76 MHz, respectively, using a 5-mm broad-banded probe.

Extraction and Fermentation of Tyrissamycin:

An aliquot of cryopreserved mycelia from *Streptomyces lividans* strain WD15684 is utilized as inoculum for the initial vegetative stage in medium V13 having the following composition: Soluble starch, 2%; glucose, 0.5%; NZ-case, 0.3%; yeast extract, 0.2%; fish meat extract, 0.5%; and calcium carbonate, 0.3%. 10 µg/ml of thiostrepton is added aseptically to each flask after autoclaving to maintain plasmid integrity. The vegetative culture is incubated at 32° C. and 230 rpm on a rotary shaker for 72-96 hours.

Following the 72-96 hour incubation, a second set of 500 ml Erlenmeyer flasks, each containing medium V13 plus 10 µg/ml thiostrepton, are seeded with 5% of the primary vegetative culture and shaken at 230 rpm for 3 days at 32° C.

Said flasks are then pooled to ensure uniformity, and 4% to 5% of the seed culture is aseptically transferred to production medium F10A. F10A broth has the following composition: Japanese soluble starch, 2.5%; dextrose, 0.2%; yeast extract, 0.5%; peptone, 0.5%; calcium carbonate, 0.3%; and distiller's solubles, 0.5%. Thiostrepton (10 µg/ml) is added post-sterilization.

The cultures are then fermented on a shaker at 230 rpm for 5 days. On the day of harvest, the contents of all flasks are pooled into a large vessel, pH and sedimentation readings are performed, and the batch is forwarded to chemistry. The production of tyrissamycin reached a maximum of about 30 µg/ml at day 5 in the production cycle.

Isolation of Tyrissamycin:

The extraction and fractionation of the above fermentation broth are monitored by the biological assay described below. Whole broth (20 liters) is stirred vigorously with ethyl acetate (6 liters) for two hours. The phases are separated and the organic layer is evaporated in vacuo to dryness. The residue (1.35 g) is dissolved in 90% aqueous methanol (200 ml) and then partitioned against hexane (3×200 ml). The aqueous methanol layer is diluted with water to a 65% MeOH solution and partitioned against pre-equilibrated chloroform (3×200 ml). The chloroform layer is pooled and evaporated to give a crude solid (322 mg). To perform column chromatography, the solid is loaded to the top of a Sephadex LH-20 column and eluted with methanol/chloroform (1:1). The eluate is collected in fractions of 10 ml and monitored for activity in the biological assay. The combined active eluate (Fraction 13-17, 130 mg) is purified by preparative thin layer chromatography (TLC; Silica Gel 60 F254, Merck, Toluene-Ethyl acetate 1:2) to yield an analytically pure sample of tyrissamycin (10 mg).

Biological Assay of Tyrissamycin:

Assays for detection and evaluation of the antibacterial activity of tyrissamycin employ various strains of *Staphylococcus aureus*. The primary biological assay system consists of *S. aureus* strain SA1.

Culture Growth and Inoculum Production:

SA1 is grown at 37° C. overnight in Antibiotic Assay Broth (BBL, Cockeysville, Md.). The culture is centrifuged at 4000 rpm for 10 minutes and the medium is decanted. Cells are resuspended in 0.9% saline. The culture is adjusted to 25% transmission (600 nm wavelength) using a Coleman Junior Spectrophotometer. This 25% working cell suspension is stored at 4° C. for use as the assay inoculum.

Biological Assay Protocol:

All biological assays employ agar diffusion techniques. Assay agar is Seed Agar (BBL) supplemented after autoclaving with 4% of phosphate-nitrate buffer, pH 7.0, and 0.3% of a 2% solution of triphenyltetrazolium chloride. For well-agar diffusion assays, assay agar is seeded with 1% of the working cell suspension of SA1. The seeded agar is poured into Petri dishes or bioassay trays and allowed to harden. Wells (7 mm diameter) are cut in the agar, and 40 μl sample aliquots are added to the wells. (For some assays, 3 μl of sample are spotted directly on the surface of the agar). Plates are incubated at 37° C. for 18-24 hours, and zones of inhibition (if any) are measured. Inhibition zone sizes correlated with the activity of tyrissamycin in various samples.

For bioautographic assays, a thin layer chromatograph (TLC) plate containing a chromatographed sample is placed in a bioassay tray. Seeded assay agar is poured over the TLC plate and allowed to harden. The bioassay tray is incubated at 37° C. for 18-24 hours and examined for the presence of inhibition zones at a position corresponding to the chemical presence of tyrissamycin.

Application of the biological assay to the detection and isolation of tyrissamycin is illustrated below.

Monitoring of Bioactivity During Initial Purification of Tyrissamycin Using a Biological Assay:

Initial purification of tyrissamycin from raw fermentation broth containing thiostrepton was accomplished using column chromatographic methods as described above. Biological assays were performed on Fractions 1-31 resulting from said chromatography. These procedures yielded a separation of tyrissamycin from other biologically active and inactive residues. Results are as follows:

| Sample | Concentration, mg/ml | Inhibition Zone, mm* |
|---|---|---|
| Fraction 1 | 1 | 7.0 |
| Fraction 2 | 1 | 9.0 |
| Fraction 3 | 1 | 10.0 |
| Fraction 4 | 1 | 16.0 |
| Fraction 5 | 1 | 20.5 |
| Fraction 6 | 1 | 20.5 |
| Fraction 7 | 1 | 19.0 |
| Fraction 8 | 1 | 15.0 |
| Fraction 9 | 1 | 13.0 |
| Fraction 10 | 1 | 12.0 |
| Fraction 11 | 1 | 11.0 |
| Fraction 12 | 1 | 9.0 |
| Fraction 13 (tyrissamycin) | 1 | 9.5 |
| Fraction 14 (tyrissamycin) | 1 | 10.5 |
| Fraction 15 (tyrissamycin) | 1 | 11.0 |
| Fraction 16 (tyrissamycin) | 1 | 10.0 |
| Fraction 17 (tyrissamycin) | 1 | 10.0 |
| Fraction 18 | 1 | 9.0 |
| Fraction 19 | 1 | 8.0 |
| Fraction 20 | 1 | 8.0 |
| Fraction 21 | 1 | 8.0 |
| Fraction 22 | 1 | 9.0 |
| Fraction 23 | 1 | 9.0 |
| Fraction 24 | 1 | 8.0 |
| Fraction 25 | 1 | 8.0 |

-continued

| Sample | Concentration, mg/ml | Inhibition Zone, mm* |
|---|---|---|
| Fraction 26 | 1 | 8.0 |
| Fraction 27 | 1 | 7.0 |
| Fraction 28 | 1 | 7.0 |
| Fraction 29 | 1 | 7.0 |
| Fraction 30 | 1 | 7.0 |
| Fraction 31 | 1 | 7.0 |

*Staphylococcus aureus strain SA1; 7 mm agar wells.

Monitoring of Bioactivity Auring Final Purification of Tyrissamycin Using a Biological Assay:

Final purification of tyrissamycin from column chromatographic fractions containing tyrissamycin was achieved as described above. Biological assays were performed on Fractions 1-4 resulting from said chromatography. These procedures yielded purified tyrissamycin Results are as follows:

| Sample | Concentration, mg/ml | Inhibition Zone, mm* |
|---|---|---|
| Fraction 1 | 5 | 7.0 |
| Fraction 2 | 5 | 8.0 |
| Fraction 3 | 5 | 8.0 |
| Fraction 4 (tyrissamycin) | 5 | 14.0 |

*Staphylococcus aureus strain SA1; 7 mm agar wells.

Figure 4:
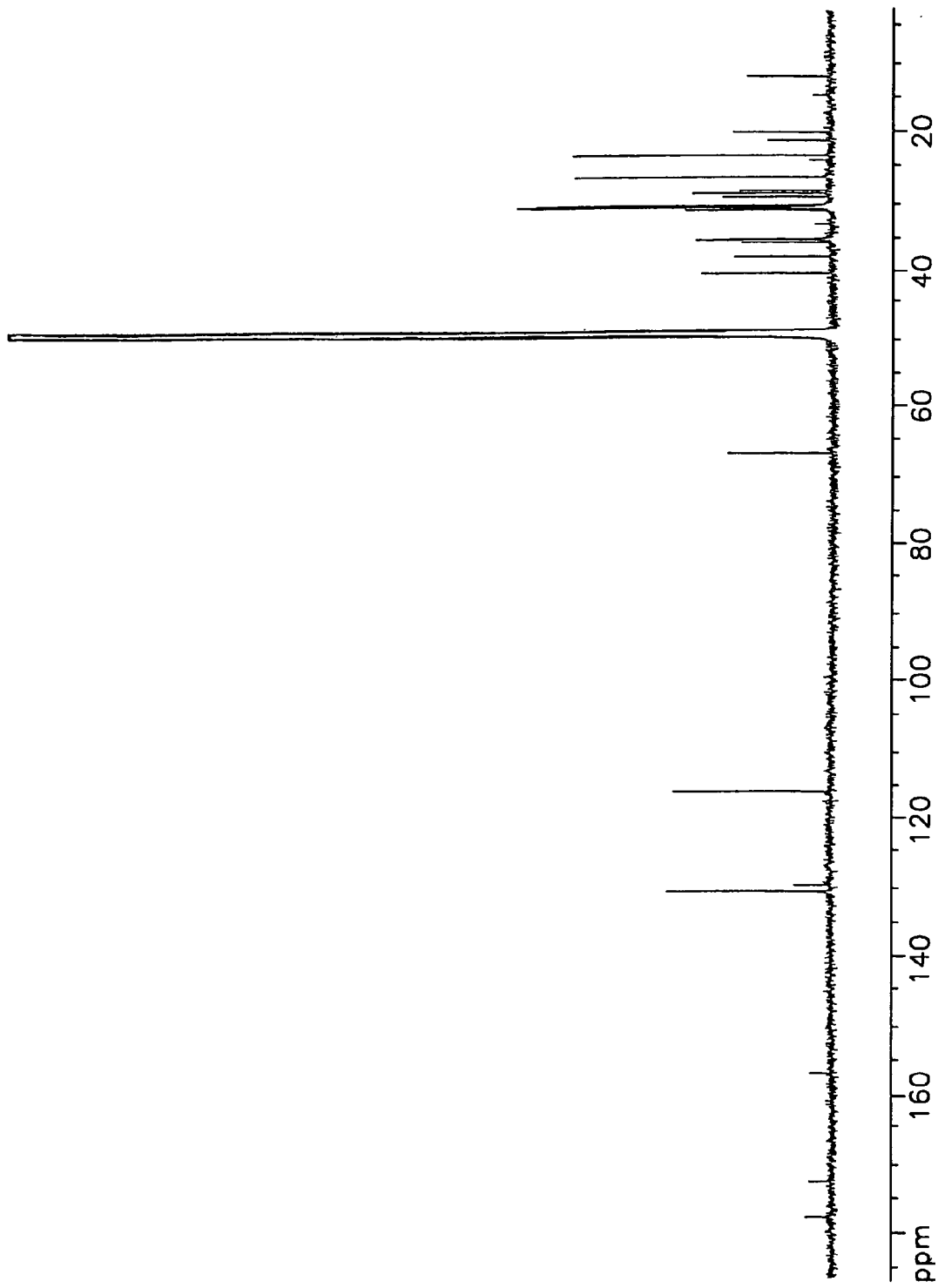
FIG. 4 shows the $^{13}C$ NMR spectrum of tyrissamycin in $CD_3OD$.

What is claimed is:

1. A process for the preparation of tyrissamycin having the following characteristics:
   (a) a white amorphous powder;
   (b) soluble in chloroform, dimethylsulfoxide and methanol, and essentially insoluble in water;
   (c) has an ultraviolet absorption spectrum when dissolved in methanol substantially as shown in FIG. 1;
   (d) has an infrared absorption spectrum (KBr) substantially as shown in FIG. 2;
   (e) has a proton magnetic resonance spectrum in $CD_3OD$ substantially as shown in FIG. 3; and
   (f) has a $^{13}C$ magnetic resonance spectrum in $CD_3OD$ substantially as shown in FIG. 4; which comprises cultivating Streptomyces lividans ATCC-202143 under submerged aerobic conditions in an aqueous nutrient medium containing assimilable sources of carbon and nitrogen until a substantial amount of tyrissamycin is produced by said organism in said culture medium.

2. The process of claim 1 which includes the step of isolating tyrissamycin from the medium in substantially purified form.

* * * * *